United States Patent
Greene

(10) Patent No.: US 9,659,150 B2
(45) Date of Patent: May 23, 2017

(54) METHOD FOR ASSESSING COGNITIVE FUNCTION AND PREDICTING COGNITIVE DECLINE THROUGH QUANTITATIVE ASSESSMENT OF THE TUG TEST

(75) Inventor: Barry Greene, Dublin (IE)

(73) Assignee: CARE INNOVATIONS, LLC, Roseville, CA (US)

( * ) Notice: Subject to any disclaimer, the term of this patent is extended or adjusted under 35 U.S.C. 154(b) by 0 days.

(21) Appl. No.: 13/554,538

(22) Filed: Jul. 20, 2012

(65) Prior Publication Data

US 2014/0025361 A1    Jan. 23, 2014

(51) Int. Cl.
| | |
|---|---|
| *G06F 19/00* | (2011.01) |
| *A61B 5/11* | (2006.01) |
| *G09B 19/00* | (2006.01) |
| *A63B 24/00* | (2006.01) |
| *A61B 5/00* | (2006.01) |

(52) U.S. Cl.
CPC ........ *G06F 19/3431* (2013.01); *G06F 19/345* (2013.01); *A61B 5/1117* (2013.01); *A61B 5/1124* (2013.01); *A61B 5/681* (2013.01); *A61B 5/6828* (2013.01); *A61B 2562/0219* (2013.01); *A63B 24/0062* (2013.01); *A63B 2024/0012* (2013.01); *A63B 2220/40* (2013.01); *A63B 2220/803* (2013.01); *A63B 2220/836* (2013.01); *G06F 19/3443* (2013.01); *G09B 19/0038* (2013.01)

(58) Field of Classification Search
CPC .......... A61B 5/1117; A61B 2562/0219; A61B 5/681; A61B 5/1124; A61B 5/6828; A63B 2220/40; A63B 2024/0012; A63B 2220/836; A63B 2220/803; A63B 24/0062; G09B 19/0038
USPC .................................. 434/81, 257, 258, 262
See application file for complete search history.

(56) References Cited

U.S. PATENT DOCUMENTS

| | | | | |
|---|---|---|---|---|
| 2001/0053883 | A1* | 12/2001 | Yoshimura et al. | 600/587 |
| 2005/0234309 | A1 | 10/2005 | Klapper | |
| 2006/0166737 | A1* | 7/2006 | Bentley | 463/30 |

(Continued)

OTHER PUBLICATIONS

Jerome H. Friedman, "Regularized Discriminant Analysis", Jul. 1988, "Journal of the American Statistical Association", pp. 1-32.*

(Continued)

*Primary Examiner* — Jack Yip
(74) *Attorney, Agent, or Firm* — Pillsbury Winthrop Shaw Pittman LLP

(57) ABSTRACT

Methods and systems may provide for cognitive decline prediction or assessment. Baseline and follow-up inertial sensor data may be received from one or more inertial sensors attached to a person. Baseline and follow-up data indicative of cognitive decline may be received from the person. An indication of cognitive decline may be determined based on the baseline and follow-up cognitive decline data. A classifier function for predicting cognitive decline may be trained with the baseline inertial sensor data and the indication of cognitive decline. A classifier function for assessing cognitive decline may be trained with the baseline inertial sensor data, a difference between the baseline inertial sensor data and follow-up inertial sensor data, and the indication of cognitive decline.

17 Claims, 8 Drawing Sheets

(56) References Cited

U.S. PATENT DOCUMENTS

2011/0092860 A1    4/2011    Salarian et al.
2012/0130266 A1    5/2012    Mathan et al.

OTHER PUBLICATIONS

Deshpande et al., "Gait speed under varied challenges and cognitive decline in older persons: a prospective study", Jul. 25, 2009, "Published by Oxford University Press on behalf of the British Geriatrics Society", pp. 509-514.*

Vellas et al., "One-Leg Balance Is an Important Predictor of Injurious Falls in Older Persons", 1997, American Geriatrics Society, pp. 735-738.*

Jennifer S. Brach, Stephanie A. Studenski, Subashan Perera, Jessie M. VanSwearingen, and Anne B. Newman, "Gait Variability and the Risk of Incident Mobility Disability in Community-Dwelling Older Adults", 2007,Journal of Gerontology: Medical Sciences, vol. 62A, No. 9, 983-988.*

Mark D. Latt, MBBS, PhD, FRACP, Stephen R. Lord, PhD, DSc, John G.L. Morris, DM (Oxon), FRACP, and Victor S.C. Fung, MBBS, PhD, FRACP, "Clinical and Physiological Assessments for Elucidating Falls Risk in Parkinson's Disease", No. 9, 2009, Movement Disorder Society, vol. 24, pp. 1280-1289.*

Greene et al., "Assessment of Cognitive Decline Through Quantitative Analysis of the Timed Up and Go Test", IEEE Transactions on Biomedical Engineering, vol. 59, No. 4, Apr. 2012, pp. 988-995.

Greene et al., "Quantitative Falls Risk Assessment Using the Timed Up and Go Test", IEEE Transactions on Biomedical Engineering, vol. 57, No. 12, Dec. 2010, pp. 2918-2926.

Greene et al., "Evaluation of Falls Risk in Community-Dwelling Older Adults Using Body-Worn Sensors", Regenerative and Technological Section/Original Paper, Gerontology 2012; 59;472-480, along with supplementary table.

Ferraris et al., "Procedure for Effortless In-Field Calibration of Three-Axis Rate Gyros and Acelerometers", Sensors and Materials, vol. 7, No. 5, 1995, 311-330.

Greene, Barry R. et al., Body-worn sensor based surrogates of minimum ground clearance in elderly falters and controls, 33rd Annual International Conference of the IEEE EMBS, Boston, Massachusetts USA, Aug. 30-Sep. 3, 2011.

Greene, Barry R. et al., Adaptive estimation of temporal gait parameters using body-worn gyroscopes, 32nd Annual International Conference of the IEEE EMBS, Buenos Aires, Argentina, Aug. 31-Sep. 4, 2010.

Greene, Barry R. et al., Falls risk assessment through quantitative analysis of TUG, Mar. 21, 2010.

Donovan, Karol J. et al., SHIMMER: A new tool for temporal Gait analysis, 31st Annual International Conference of the IEEE EMBS, Minneapolis, Minnesota, USA, Sep. 2-6, 2009.

Doheny, Emer P., et al., A single gyroscope method for spatial gait analysis, 32nd Annual International Conference of the IEEE EMBS, Buenos Aires, Argentina, Aug. 31-Sep. 4, 2010.

McGrath, Denise et al., Estimation of minimum ground clearance (MGC) using body-work inertial sensors, Journal of Biomechanics 44 (2011), pp. 1083-1088.

Greene, Barry R. et al., An adaptive gyroscope-based algorithm for temporal gait analysis, Med Biol Eng Computn Nov. 2010, vol. 48, pp. 1251-1260.

Extended European Search Report issued Jun. 8, 2016 in EP Application No. 13177483.8.

Patel S. et al., "Monitoring Motor Fluctuations in Patients with Parkinson's Disease Using Wearable Sensors", IEEE Transactions on Information Technology in Biomedicine, IEEE Service Center, Los Alamitos, CA, US, vol. 13, No. 6, Nov. 2009, pp. 864-873.

\* cited by examiner

| Feature | |
|---|---|
| Temporal parameters | Turn parameters |
| Cadence (step/min) | Number steps taken for subject to turn |
| CV double support (%) | Ratio of steps taken to turn to the time taken to turn |
| CV single support (%) | |
| CV stance time (s) | Time taken to turn (s) |
| CV step time (s) | Turn angular velocity (deg/s) |
| CV stride time (s) | Turn mid-point time (s) |
| CV swing time (s) | |
| Mean double support (%) | Angular velocity parameters |
| Mean mid-swing points (deg/s) | CV X-axis angular velocity (deg/s) |
| Mean single support (%) | CV Y-axis angular velocity (deg/s) |
| Mean stance time (s) | CV Z-axis angular velocity (deg/s) |
| Mean step time (s) | Max X-axis angular velocity (deg/s) |
| Mean stride time (s) | Max X-axis angular velocity x Height |
| Mean swing time (s) | Max Y-axis angular velocity (deg/s) |
| No. gait cycles | Max Y-axis angular velocity x Height |
| No. steps | Max Z-axis angular velocity (deg/s) |
| Range of mid-swing points (deg/s) | Max Z-axis angular velocity x Height |
| | Mean X-axis angular velocity (deg/s) |
| Return time (s) | Mean X-axis angular velocity x Height |
| Time taken to stand (s) | Mean Y-axis angular velocity (deg/s) |
| TUG recording time (s) | Mean Y-axis angular velocity x Height |
| Walk time (s) | Mean Z-axis angular velocity (deg/s) |
| Walk-time ratio | Mean Z-axis angular velocity x Height |
| | Min X-axis angular velocity (deg/s) |
| Spatial parameters | Min X-axis angular velocity x Height |
| Stride length (cm) | Min Y-axis angular velocity (deg/s) |
| Stride velocity (cm/s) | Min Y-axis angular velocity x Height |
| CV stride length (%) | Min Z-axis angular velocity (deg/s) |
| CV stride velocity (%) | Min Z-axis angular velocity x Height |

FIGURE 3A

METHOD FOR ASSESSING COGNITIVE FUNCTION AND PREDICTING COGNITIVE DECLINE THROUGH QUANTITATIVE ASSESSMENT OF THE TUG TEST

BACKGROUND

Technical Field

Embodiments generally relate to predicting or assessing cognitive decline in older adults.

Discussion

With recent improvements in living standards along with advances in modern medicine, people in developed countries are living far longer than in previous eras. Cognitive decline in older adults represents a major clinical challenge, presenting a huge societal burden with enormous direct and indirect social and economic costs. For example, the global prevalence of Alzheimer's disease is estimated at 24 million people worldwide. Early detection of cognitive decline could lead to more effective clinical intervention and treatments that might delay the onset of cognitive decline.

SUMMARY

An embodiment of this invention relates to associating parameters that measure a person's movement (e.g., gait parameters) with parameters that measure a person's global cognitive function (e.g., mini-mental state exam (MMSE) score), and more specifically with a decline in cognitive function. A cognitive decline may range from mild cognitive impairment to dementia or Alzheimer's Disease. A person's gait parameters and variability of such parameters during walking may reflect the health of a person's neuromuscular system. A disturbance in the person's gait or another decline in motor function may precede an onset of cognitive decline. Thus, the person's movement parameters may be used to predict whether the person will experience cognitive decline or to assess whether the person has undergone cognitive decline.

In an embodiment, predicting whether a person will undergo cognitive decline may be based on baseline inertial sensor data collected from the person. In an embodiment, if both baseline (e.g., initial) and follow-up (e.g., subsequent) inertial sensor data are available, the baseline inertial sensor data and changes between the baseline and follow-up inertial sensor data may be used to assess whether the person has experienced cognitive decline in the time between the baseline and follow-up evaluation. The follow-up inertial sensor data may be collected from the same person days, weeks, months, or years after the baseline inertial sensor data was collected. The prediction or assessment may rely on a classifier function that automatically classifies baseline inertial sensor data, follow-up inertial sensor data, or both as being associated with intact cognitive function or with a decline in cognitive function. If only baseline inertial sensor data is available, a classifier function may predict from the data whether cognitive decline will occur. If both baseline and inertial sensor data are available, a classifier function may still assess whether cognitive decline has occurred, thus allowing even those without expertise in cognition to obtain an assessment of a person's cognitive status, or to prompt further investigation into a person's cognitive status.

In an embodiment of this invention, the inertial sensor data may be collected as a person is performing a "timed up and go" (TUG) test. The test measures how quickly a person can stand up from a chair, walk 3 metres, and return to his or her original position on the chair. An inertial sensor, such as a combination of a gyroscope and accelerometer, may be attached to the person and may collect inertial sensor data during the TUG test. The test is quick to administer, requires no special equipment or training, and can be easily included as part of a routine medical examination. A range of parameters, referred to as quantitative TUG (qTUG) parameters, may be determined from sensor data obtained during the TUG test. The parameters may be categorized into temporal gait parameters, spatial gait parameters, turn parameters, and angular velocity parameters, and are discussed below in more detail.

In an embodiment, a classifier function may be generated to predict cognitive decline based on baseline inertial sensor data, such as baseline, qTUG, parameters. Generating the function may be part of a supervised pattern recognition technique in which the classifier function is trained to associate known inertial sensor data obtained from a sample of people with known cognitive decline indicators of those people. The trained classifier function may then be used to predict whether a person outside the sample will experience cognitive decline based on inertial sensor data collected from him or her.

For example, a regularized discriminant classifier function may be generated based on baseline inertial sensor data collected from the person and based on baseline and follow-up MMSE scores collected from the person. The follow-up occurs at a subsequent time (e.g., 2 years) after the baseline evaluation. One or more qTUG parameters may be calculated from the baseline inertial sensor data and used as an input to the classifier function. If the person's MMSE score decreased by three or more from baseline to follow-up, the person may be considered to have undergone a cognitive decline. In that instance, the classifier function may be trained to associate values of the one or more qTUG parameters with a prediction of cognitive decline. If the person's MMSE score had a smaller decrease or did not decrease, the classifier function may be trained to associate values of the one or more qTUG parameters with a prediction of no cognitive decline. The classifier function may be trained with qTUG parameters and MMSE scores derived from a sample of multiple people. The trained regularized discriminant classifier function may be used to predict whether other people will experience cognitive decline based on qTUG parameter values derived from inertial sensor data of such other people.

In an embodiment, input to a classifier function may also include clinical parameters, such as age, height, grip strength, Berg Balance Scale (BBS) score, or manual TUG time.

In an embodiment, a classifier function may be generated to assess whether cognitive decline has occurred. The classifier function may allow non-experts to assess cognitive decline based simply on baseline and follow-up inertial sensor data collected from the person. The classifier function may be trained using both baseline and follow-up inertial sensor data and using baseline and follow-up cognitive function data. For example, baseline qTUG parameter values may be calculated from the baseline inertial sensor data and $\Delta$qTUG parameter values may be calculated from changes between the baseline and follow-up inertial sensor data. If the person's MMSE score decreased by three or more, the classifier function may be trained to associate the qTUG and $\Delta$qTUG parameter values with an assessment of cognitive decline. If the person's MMSE score decreased by less or did not decrease, the classifier function may be trained to associate the qTUG and $\Delta$qTUG parameter values with an assessment of no cognitive decline. After the classifier function has been trained, the classifier function may use baseline and follow-up inertial sensor data collected from another person to assess whether that person has experienced cognitive decline in the time between the baseline and follow-up evaluations. The classifier function allows a non-expert to assess cognitive decline based simply on inertial sensor data and relieves the non-expert from having to conduct a separate test, such as an MMSE test.

These and other embodiments are described in more detail below.

BRIEF DESCRIPTION OF THE DRAWINGS

The various features of the embodiments will become apparent to one skilled in the art by reading the following specification and appended claims, and by referencing the following drawings, in which:

FIG. 3A illustrates example parameters for which values are calculated from inertial sensor data.

DETAILED DESCRIPTION

Figure 1:
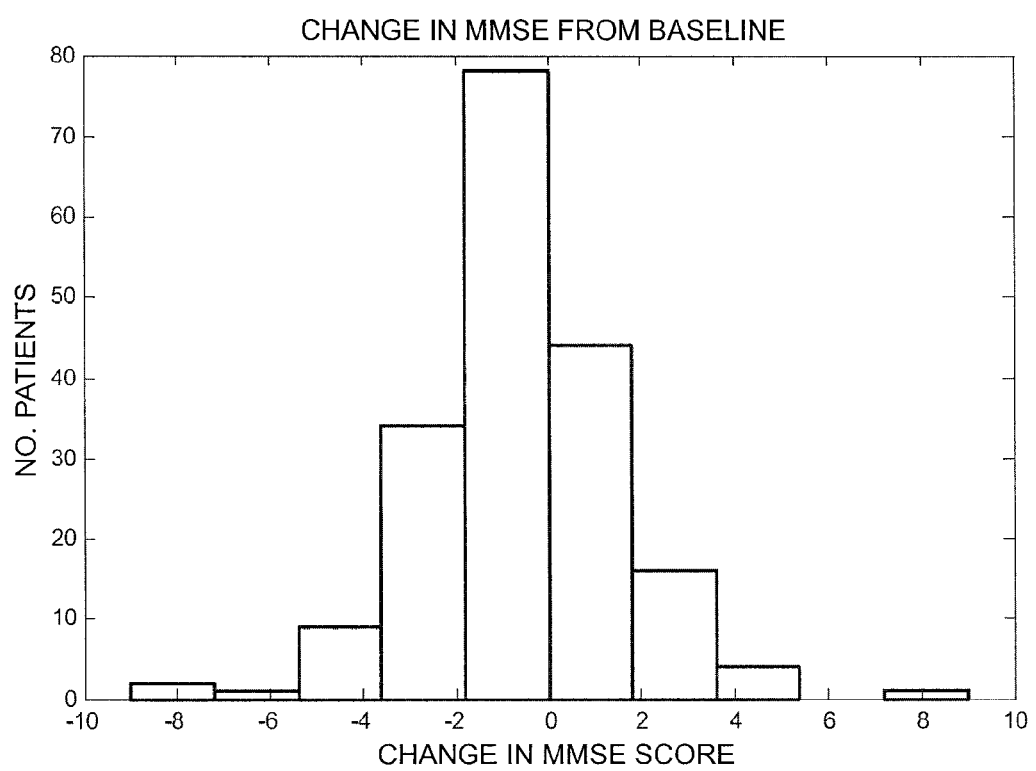
FIG. 1 illustrates a histogram of example changes in MMSE scores from a baseline assessment to a future, follow-up assessment.

Embodiments may provide for a system and method for generating classifier functions that predict cognitive decline or for generating classifier functions that assess cognitive decline. In an embodiment, the classifier functions may be trained based on a person's movement, changes in the person's movement over time, and changes in the person's score on the Mini-mental state exam, or MMSE score. Example changes in people's MMSE scores over a two-year period are illustrated in FIG. 1. In an embodiment, a decrease of three or more in a person's MMSE score may indicate cognitive decline in the person, while a smaller decrease may indicate that the person's cognition is still intact.

Figure 2:
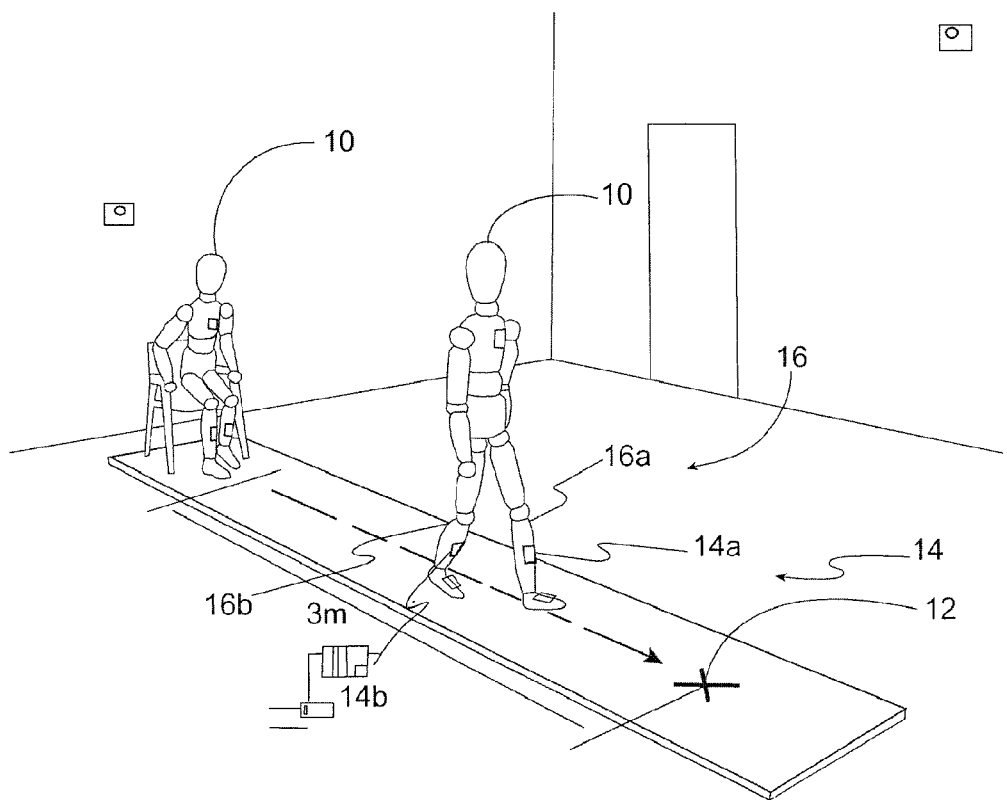
FIG. 2 illustrates a perspective view of an example of an individual performing the timed up and go (TUG) test.

In an embodiment, inertial sensor data that capture the person's movement may be obtained from one or more inertial sensors attached to a person. FIG. 2a illustrates inertial sensor data being collected by inertial sensors 14a and 14b attached to person 10 as the person is performing a "timed-up and go" (TUG) test. During the TUG test, the person is asked to get up from a standard chair, walk a distance (e.g., 3 meters), turn at a designated spot 12, return to the seat, and sit down. The inertial sensors 14a and 14b may collect, for example, accelerometer or gyroscope data. From such data, various quantitative parameters, or qTUG parameters, may be calculated. Such qTUG parameters may represent aspects of the person's balance or posture, which may be associated with a person's cognitive status or with cognitive decline in the person.

Inertial sensors 14a and 14b may each include a tri-axial accelerometer and tri-axial gyroscope, and may each be sampled at 102.4 Hz. Each sensor may be attached to a mid-point of an anterior shank 16a or 16b of person 10 participating in the TUG test. Video data of the test may be synchronously acquired to visually ensure that only sensor data from valid TUG tests are used in an analysis of inertial sensor data.

Parameters derived from the inertial sensor data, such as qTUG parameters, may include a temporal gait parameter, a spatial gait parameter, a turn parameter, an angular velocity parameter, or any other parameter. FIG. 3A illustrates example qTUG parameters that may be derived from inertial sensor data. Calculation of one or more qTUG parameters may be based on initial contact points (also known as heel strike points) and terminal contact (also known as toe off points) points with the ground. Such contact points may be adaptively determined from minima values in angular velocity signals received from the inertial sensors. Each terminal contact point may be followed by a mid-swing point that can be identified via a maximum value in the signal. Each mid-swing point may be followed by an initial contact point that is reflected in another minimum angular velocity value. Calculation of various other qTUG parameters, such as cadence, double support percentage, single support percentage, stance time, step time, stride time, swing time, and any other qTUG parameter is explained in more detail in U.S. patent application Ser. No. 13/186,709, entitled "A Method for Body-Worn Sensor Based Prospective Evaluation of Falls Risk in Community-Dwelling Elderly Adults," filed Jul. 20, 2011, the entire content of which is incorporated by reference; and in U.S. patent application Ser. No. 12/782,110, entitled "Wireless Sensor Based Quantitative Falls Risk Assessment," filed May 18, 2010, the entire contents of which is incorporated herein by reference. Further, qTUG parameters may include statistical measures, such as a mean, minimum, or coefficient of variability (CV) of other qTUG parameters.

For example, as discussed in the above applications, the parameter of step time may be calculated as a time between an initial contact point on one foot and an initial contact point on another foot. The parameter walk ratio may be calculated as a ratio of time between when a clinician says 'go' in a TUG test to a median gait event of the TUG test and the time between the median event to the end of the TUG test. The parameter turn-end time may be calculated as a time from a median gait event of the TUG test to the end of the test. The parameter turn-start time may be calculated as the time between when the clinician says 'go' to the median gait event of the TUG test. The parameter of number of gait cycles may be calculated as a number of initial contact points detected from angular velocity data during a TUG test minus one (i.e., the number of complete gait cycles). The parameter single support percentage for a foot may be calculated as a swing duration of the other foot expressed as a percentage of gait cycle time. The single support percentage, data for each foot may be merged. The parameter double support percentage may be calculated as the percentage of each gait cycle during which both feet are in contact with the ground, where the gait cycle may include the time between successive initial contact points.

Although embodiments of this application discusses inertial sensor data as inputs to a classifier function, the classifier function may further be based on clinical parameters such as a person's height, age, grip strength, BBS score, CESD-8 score, or manual TUG time. The person's grip, which may be used as a surrogate measure for his strength or frailty, may be measured using a handheld dynamometer, for example. The person's Berg Balance Scale score, or BBS, score, may be evaluated by performing the tasks detailed in the Berg balance scale. The person's Center for Epidemiological Studies Depression, or CESD-8, score may be used to evaluate the person's mood. The manual TUG time may be measured as the time for the person to complete the TUG test (i.e., time to stand up, walk, turn at designated spot, and return to seat).

The qTUG parameters and other (e.g., clinical) parameters may be used as features that are associated with whether a person experiences or has experienced cognitive decline. For example, a classifier function, or model, may be trained using supervised pattern recognition methods to associate values of inertial sensor parameters with measurements indicative of a person's cognitive decline. The measurements indicative of cognitive decline may include a person's Mini-mental state exam (MMSE) score. In an embodiment, a decrease of three or more in a person's MMSE score, from a baseline to a follow-up test, may be considered an indication of cognitive decline in the person. In another embodiment, another threshold (e.g., two, four, five) may be used. The classifier function may be trained to associate certain values of input parameters with an indication of cognitive decline and to associate certain values of the input parameters with an indication of no cognitive decline.

Figure 3B:
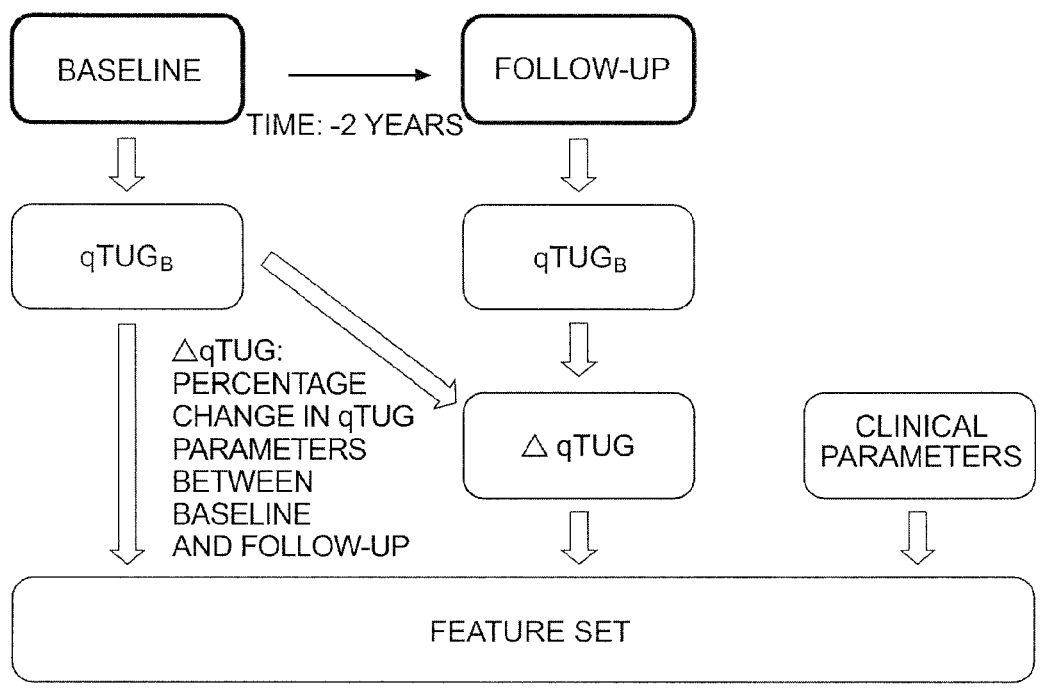
FIG. 3B illustrates example combinations of parameters for generating a feature set used by a classifier function to predict or assess cognitive decline.

FIG. 3B illustrates various ways for combining qTUG parameters and other parameters into a set of parameters, or feature set, that are used as input parameters of a classifier function. In an embodiment, various baseline qTUG parameters, or $qTUG_B$ parameters, may form a feature set for a classifier function that predicts cognitive decline. The classifier function may be trained with values of parameters in the feature set, and may later predict whether a person will experience cognitive decline based on values of those parameters as calculated from that person's inertial sensor data.

In an embodiment, various $qTUG_B$ parameters may be combined with $\Delta qTUG$ parameters to form a feature set. A $\Delta qTUG$ parameter may be calculated as a difference between a follow-up qTUG, or $qTUG_F$ parameter, and its corresponding baseline, $qTUG_B$ parameter. The feature set may be used by a classifier function to assess whether a person has undergone cognitive decline. Although both baseline and follow-up data are already known in this embodiment, the classifier function allows even a non-expert to make use of the data by deriving a cognitive decline indication from the baseline and follow-up sensor data.

As illustrated in FIG. 3B, the time periods between when baseline data and follow-up data were obtained may be separated by several years. In another embodiment, they may be separated by one or more days, weeks, or months. As further illustrated in the figure, a feature set may also include clinical parameters, such as a person's age (at either the baseline or follow-up evaluation), height, weight, grip strength, manual TUG time, BBS score, or CESD-8 assessment.

Figure 3C:
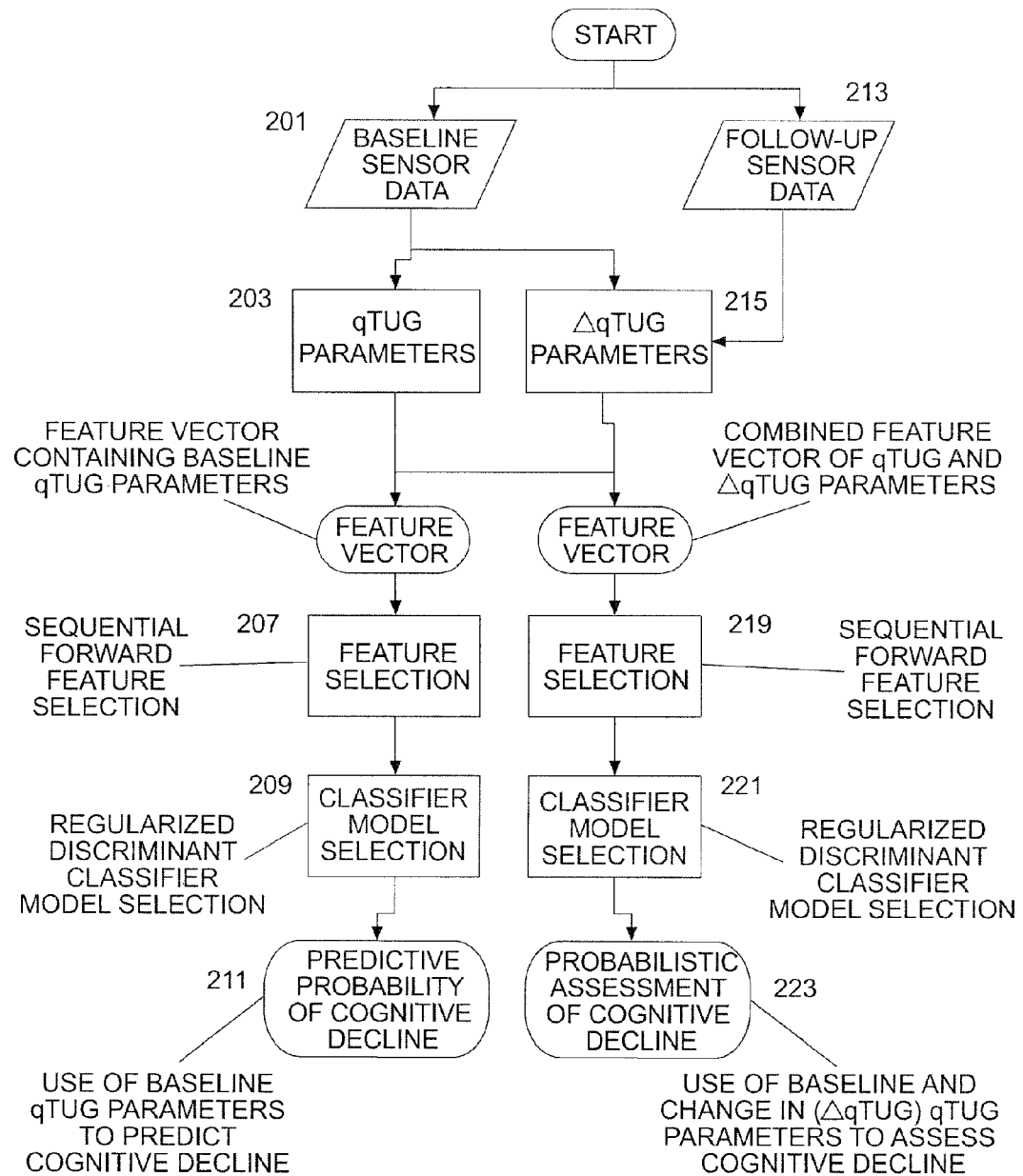
FIG. 3C illustrates various example operations for generating a classifier function for predicting whether cognitive decline will occur or for generating a classifier function for assessing whether cognitive decline has occurred.

FIG. 3C illustrates more detailed operations for generating a classifier function for predicting cognitive decline and for generating a classifier function for assessing cognitive decline. At operation 201, baseline inertial sensor data may be received. The inertial sensor data may be received, for example, via a wireless connection from one or more inertial sensors, such as an accelerometer and a gyroscope. The inertial sensor data may include angular velocity data, orientation data, acceleration data, or any other inertial sensor data. In an embodiment, the baseline inertial sensor data may be received during performance of a TUG test. The one or more inertial sensors may be worn by or otherwise attached to the person performing the test.

At operation 203, one or more qTUG parameter values, such as values of parameters shown in FIG. 3A, may be calculated. In an embodiment, the values may be calculated on the one or more sensors and then transmitted by the one or more sensors. In an embodiment, the values may be calculated by one or more processors that receive the inertial sensor data from the one or more sensors. In an embodiment, the one or more sensors or one or more processors may allow a user to configure which parameter values are to be calculated. The calculated parameter values may be arranged as a set or vector of feature values for a classifier function. In an embodiment, the feature vector or feature set may include all parameters that were calculated.

At operation 207, as part of training the classifier function, feature selection may be performed on the feature vector or feature set to select a subset of features that the classifier function will use as input. The feature selection may, for example, start with an empty set and add features to the set from the feature vector until accuracy of the classifier function stops increasing. The added features may form the subset of features that are selected. In a more specific example, sequential forward feature selection and a grid search may be performed to determine an optimal subset of features and other optimal values used by the classifier function. During the selection, a function may be evaluated using 10-fold cross validation to ensure an unbiased estimate of generalized classifier performance. A one-sided t-test may be used to determine if the classification result obtained for each function is significantly better than those obtained using other functions.

At operation 209, a type of the classifier function, or model, may be selected. For example, the classifier function may be a regularized discriminant classifier function, or may be any other classifier function.

The selected classifier function may be trained to predict cognitive decline based on values of the selected subset of features, or parameters. In an embodiment, a supervised pattern recognition method may be used in which the classifier function may be trained with sensor data labeled according to cognitive status (e.g. cognitively declined, cognitively intact). For example, baseline and follow-up MMSE scores may be available for the people who generated the inertial sensor data. Whether a person in that sample has had cognitive decline may be based on, for example, whether his or her MMSE score decreased by three or more from baseline to the follow-up evaluation. The classifier function may be trained to associate values of the selected subset corresponding to each person with the indication of whether that person had a cognitive decline. If the classifier function is a regularized discriminant classifier, the training may include finding optimal $\lambda$ and $r$ values for the classifier.

At operation 211, the classifier function may be used to predict cognitive decline. For example, at a baseline evaluation, a caregiver may use an inertial sensor to collect inertial sensor data from a new patient. Values for the selected subset of features, or parameters, may be calculated. The values may be inputted into the trained classifier function, which may predict based on the values whether the new patient will undergo cognitive decline in the general future or, for example, within two years (i.e., the time between the baseline evaluation and the follow-up evaluation). In an embodiment, the prediction of cognitive decline may be a proxy for a prediction that a MMSE score of the new patient would decrease by more than three within, for example, two years.

FIG. 3C illustrates additional operations for generating a classifier function for assessing whether cognitive decline has occurred. For example, during a follow-up evaluation that occurs two years after a baseline evaluation, the classifier function may be used to assess whether a person has experienced cognitive decline within the last two years.

At an operation 213, follow-up inertial sensor data may be obtained from one or more inertial sensors attached to a person. The one or more sensors may include a sensor attached to the person's left leg, a sensor attached to the person's right leg, and a sensor attached to the person's lower back. The follow-up inertial sensor data may include angular velocity data, acceleration data, orientation data, or any other inertial sensor data.

At operation 215, a numerical difference in the qTUG parameters, or ΔqTUG parameters, may be calculated. The ΔqTUG parameters may calculate a difference in values of $qTUG_B$ baseline parameters and values of their corresponding $qTUG_F$ follow-up parameters. The calculated values of both $qTUG_B$ parameters and ΔqTUG parameters may be arranged as a set or vector of feature values for a classifier function. In an embodiment, the feature vector or feature set may include all $qTUG_B$ and ΔqTUG parameters that were calculated.

At operation 219, feature selection may be performed on the above feature vector or feature set to select a subset of features that the classifier function will use as input. The feature selection may, for example, start with an empty set and add features to the set from the feature vector until accuracy of the classifier function stops increasing. The added features may form the subset of features that are selected. In a more specific example, sequential forward feature selection and a grid search operation may be performed to determine an optimal subset of features and other optimal values used by the classifier function. During the selection, a function may be evaluated using 10-fold cross validation to ensure an unbiased estimate of generalized classifier performance. A one-sided t-test may be used to determine if the classification result obtained for each function is significantly more accurate than those obtained using other functions.

At operation 221, a classifier function type, such as a regularized discriminant classifier function or any other classifier function, may be selected.

The selected classifier function may be trained to assess cognitive decline based on values of the selected subset of features, or parameters. In an embodiment, a supervised pattern recognition technique may be used in which the classifier function may be trained with known cognitive decline data. For example, baseline and follow-up MMSE scores may be available for the people who generated the inertial sensor data. Whether a person in that sample has had cognitive decline may be based on, for example, whether his or her MMSE score decreased by three or more. The classifier function may be trained to associate $qTUG_B$ and ΔqTUG values of the selected subset corresponding to each person with the indication of whether that person experienced a cognitive decline. If the classifier function is a regularized discriminant classifier, the training may include finding optimal λ and r values for the classifier.

At operation 223, the trained classifier function may be used to assess whether another person has undergone cognitive decline. In an embodiment, when inertial sensor data is being collected from a patient to evaluate his or her cognitive status, it may be determined that baseline inertial sensor data from the patient has also been previously collected. If they have, the current inertial sensor data may be compared with the baseline inertial sensor data to generate $qTUG_B$ and ΔqTUG parameter values. The values may be inputted into the trained classifier function, which may assess based on the input values whether the patient has undergone cognitive decline since the baseline evaluation. In an embodiment, the assessment of cognitive decline may be a proxy for an assessment that a current MMSE score of the patient would be less than a baseline MMSE score of the patient by three or more.

Table 1 illustrates example differences in values of clinical parameters between a sample of people who experienced cognitive decline and a sample of people who did not experience cognitive decline.

TABLE 1

| Variable | Cognition unchanged (ΔMMSE <3, N = 158) | Cognitive decline (ΔMMSE ≥3, N = 22) |
|---|---|---|
| N (Male/Female) | 47/111 | 9/13 |
| Age (yrs) | 69.97 ± 6.44 | 72.86 ± 7.14 |
| Height (cm) | 167.41 ± 8.79 | 164.81 ± 9.85 |
| Weight (kg) | 75.13 ± 14.10 | 74.40 ± 14.38 |
| Grip (lbs) | 55.63 ± 21.24 | 55.02 ± 23.41 |
| MMSE at Baseline | 28.10 ± 1.57 | 28.59 ± 1.53 |
| MMSE at Follow-up | 24.7 ± 2.2 | 28.18 ± 1.5 |
| Manual TUG time (s) | 8.64 ± 2.61 | 8.73 ± 1.61 |
| Berg Balance Scale (BBS) score | 53.59 ± 3.87 | 52.91 ± 4.74 |
| Center for Epidemiological Studies Depression (CESD-8) scale | 1.40 ± 1.70 | 1.36 ± 1.79 |

Figure 4:
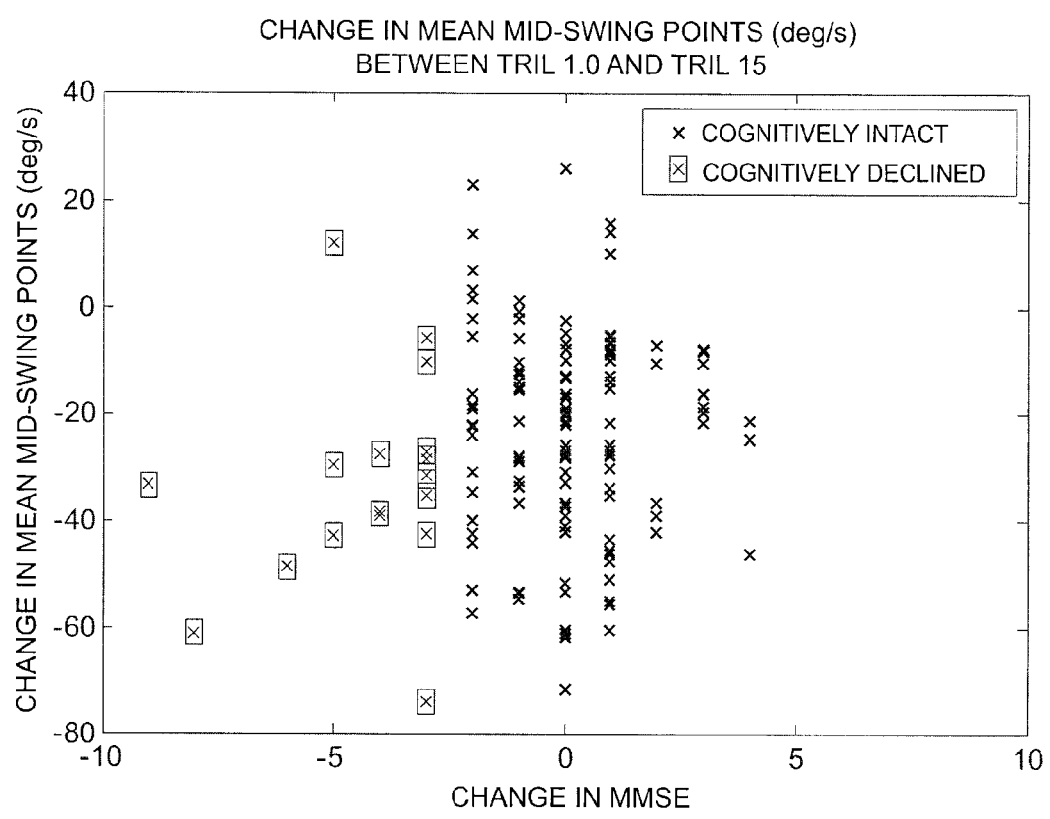
FIG. 4 graphically illustrates a relationship of changes in mean mid-swing points and changes in MMSE scores.

A Mann-Whitney version of the Wilcoxon rank sum test may be conducted to determine whether any parameter show a statistically significant difference in value between a person who experienced cognitive decline and a person who did not. In one example, one $qTUG_B$ parameter, the range of Y-axis angular velocity value at mid-swing points, showed a significant (i.e., p<0.05) association with cognitive decline. This parameter measures a range or variability in maximum speed of shank movements between individual strides. Further in the example, five ΔqTUG parameters showed significant association with cognitive decline: Δ range of the Y-axis angular velocity values at mid-swing points, Δ (i.e. numerical difference) in the turn mid-point time, Δ in the mean angular velocity at mid-swing points, Δ in the number of steps taken to complete the TUG test, and Δ in the coefficient of variation (CV) of the X-axis angular velocity. FIG. 4 graphically illustrates example change in mean angular velocity values at mid-swing points in relation to changes in MMSE scores. Thus, change in gait and other movement parameters may be associated with a change in cognitive function.

Table 2 illustrates example parameters that may be selected as input parameters of a classifier function. The example classifier function is a regularized discriminant classifier. Table 2 illustrates example qTUG parameters, clinical parameters, and regularization parameters (e.g., λ and r) for the regularized discriminant classifier function. Models 1, 3, and 4 are classifier functions that may be used to predict cognitive decline. Model 2 is a classifier function that may be used to assess whether a person has undergone a decline in cognitive function. Models 3 and 4 may be used as benchmarks against which the accuracy of models 1 and 2 can be compared.

TABLE 2

| Model 1 (baseline parameters only) | Model 2 (baseline and change from baseline parameters) | Model 3 Age only | Model 4 Baseline manual TUG |
|---|---|---|---|
| $\lambda = 0.3, r = 0$ | $\lambda = 0.1, r = 0.1$ | $\lambda = 1, r = 0.4$ | $\lambda = 1, r = 0$ |
| Mean step time (s) | Mean step time (s) | Age at baseline | Manual TUG time at baseline |
| Range of mid-swing points (deg/s) | Min Z-axis ang. vel. (deg/s) | | |
| Walk Ratio | Change in CV double support (%) | | |
| Turn-End time (s) | Change in Mean single support (%) | | |
| CV X-axis ang. vel. (%) | Change in Mean step time (%) | | |
| CV Z-axis ang. vel. (%) | Change in CV Y-axis ang vel (%) | | |
| Height (cm) | Change in no. gait cycles (%) | | |
| Grip (lbs) | Change in range of mid-swing points (%) | | |
| | Change in Turn-Start Time (%) | | |
| | Change in Turn-End time (%) | | |
| | Change in CV X-axis ang. vel. (%) | | |
| | Change in Min Z-axis ang. vel. (%) | | |

Table 3 illustrates example values of metrics that evaluate the performance of the classifier functions of the four models. The evaluation may be performed using cross-validation.

TABLE 3

| | Model 1 | Model 2 | Model 3 | Model 4 |
|---|---|---|---|---|
| Acc (%) | 75.51 | 88.60 | 59.04 | 58.90 |
| Sens (%) | 66.25 | 74.38 | 62.50 | 56.25 |
| Spec (%) | 76.72 | 90.50 | 58.58 | 59.25 |
| PPV (%) | 27.18 | 51.07 | 16.75 | 15.54 |
| NPV (%) | 94.55 | 96.36 | 92.14 | 91.04 |
| ROC area | 0.80 | 0.94 | 0.61 | 0.54 |

A classification accuracy (ACC) of a function may be calculated as the percentage of people correctly classified by the function as having cognitively declined or as having remained cognitively intact. A sensitivity (Sens) may be calculated as the percentage of cognitively declined people who were correctly classified as such. A specificity (Spec) may be calculated as the percentage of people who were cognitively intact at baseline and were correctly identified as such. A positive predictive value (PPV) may be calculated as the proportion of people who, out of those classified as cognitively declined by the function, have actually cognitively declined. A negative predictive value (PPV) may be calculated as the proportion of people who, out of those classified as cognitively intact by the function, are actually cognitively intact. An area under a receiver operating characteristic curve (ROC area) may be calculated as an area under a curve that plots sensitivity (Sens) as a function of specificity (Spec). The ROC area may provide an overall index of diagnostic performance.

In the example, the classifier function of model 1 predicted final cognitive status (e.g., whether there will be cognitive decline) with a 75.51% accuracy. The function of model 2 assessed final cognitive status with an accuracy of 88.6%. For comparison, the function of model 3, which is based on a person's age at baseline, predicted cognitive status with an accuracy of 59.04%. Similarly, model 4 predicted cognitive status based on manual TUG time at baseline with an accuracy of 58.90%.

Figure 5:
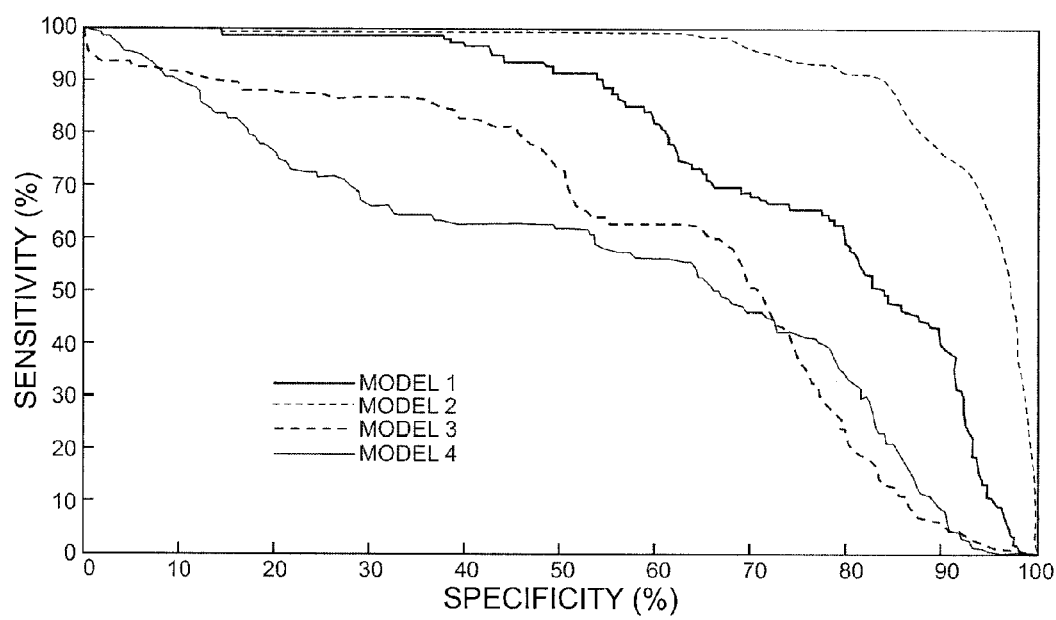
FIG. 5 illustrates example sensitivity and specificity values of various classifier functions.
Figure 6:
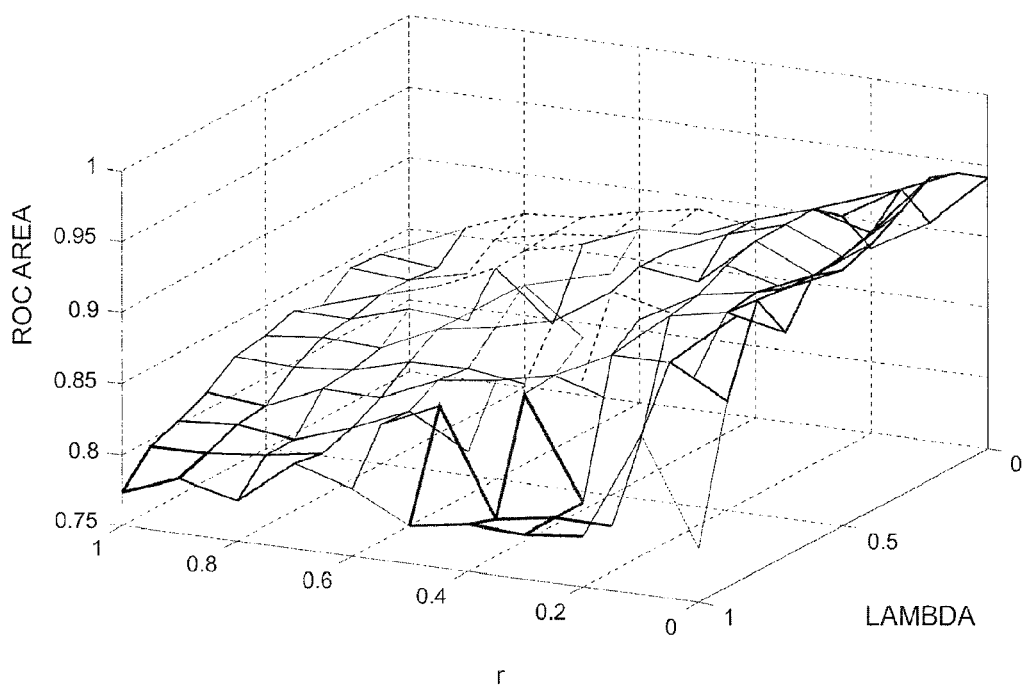
FIG. 6 illustrates example values of a metric of accuracy of a classifier function based on parameter values of the classifier function.

Each example regularized discriminant classifier function may be obtained by choosing a pair of regularization parameters, $\lambda$ and r, that yield a maximum area under a ROC curve, which is a curve in which sensitivity is a function of specificity. Example ROC curves for the functions of the four models are illustrated in FIG. 5. In the example, model 2 yielded the best ROC area of 0.94. FIG. 6 illustrates an example relationship between ROC area for model 2 and values of $\lambda$ and r.

Thus, classifier functions may be trained to allow non-experts, such as caretakers, to predict or assess the cognitive abilities of their patients. An early prediction or assessment of a cognitive impairment (e.g., dementia) may allow for early clinical intervention that may more effectively treat or delay the cognitive impairment.

Although embodiments of this application discuss two evaluations, i.e. a baseline evaluation and a follow-up evaluation, data from additional evaluations may be included in a supervised pattern recognition method. For example, inertial sensor data may be collected from a person during many consecutive days, weeks, or months. Parameters based on data from each of the time periods and parameters based on differences among such data may be used in the supervised pattern recognition. In an embodiment, trajectories of physical and cognitive decline and frailty may be recognized.

Embodiments of the present invention are applicable for use with all types of semiconductor integrated circuit ("IC") chips. Examples of these IC chips include but are not limited to processors, controllers, chipset components, programmable logic arrays (PLA), memory chips, network chips, and the like. In addition, in some of the drawings, signal conductor lines are represented with lines. Some may be thicker, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments of the present invention are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments of the invention. Further, arrangements may be shown in block diagram form in order to avoid obscuring embodiments of the invention, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments of the invention, it should be apparent to one skilled in the art that embodiments of the invention can be practiced without, or with variation of, these specific details. The description is thus to be regarded as illustrative instead of limiting.

The term "coupled" is used herein to refer to any type of relationship, direct or indirect, between the components in question, and may apply to electrical, mechanical, fluid, optical, electromagnetic, electromechanical or other connections. In addition, the terms "first", "second", etc. are used herein only to facilitate discussion, and carry no particular temporal or chronological significance unless otherwise indicated.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications, will become apparent to the skilled practitioner upon a study of the drawings, specification, and following claims.

I claim:

1. A computer-readable non-transitory medium comprising computer-readable code physically embodied thereon which, when executed by a processor, causes the processor to perform a method comprising:
receiving inertial sensor data directly from one or more inertial sensors attached to a person's shank that performs a quantitative timed-up-and-go (QTUG) test, the inertial sensor data being measured by the one or more inertial sensors and including shank angular velocity data comprising measured gait parameters related to the person sitting, walking, and turning;
receiving, at a time subsequent to receiving the inertial sensor data from the QTUG test, additional inertial sensor data indicative of cognitive function of the person directly from the one or more inertial sensors, including shank angular velocity data comprising gait parameters related to the person sitting, walking, and turning measured during a subsequent QTUG test;
determining an indication of cognitive decline in the person based on a difference between the inertial sensor data indicative of cognitive function and the received additional inertial sensor data including a difference between the gait parameters;
generating a classifier function that associates the received inertial sensor data with the determined indication of cognitive decline in the person as a prediction for cognitive decline in other persons;
after generation of the classifier function, collecting inertial sensor data directly from the one or more inertial sensors from another person that performs the QTUG test;
using the generated classifier function, associating the collected inertial sensor data from the QTUG test from the another person to an indication of cognitive decline in the another person; and
providing, using the association from the generated classifier function, to a user a prediction of whether the another person will experience cognitive decline based on the inertial sensor data collected from the another person,
wherein the prediction provided to the user comprises a classification of the another person as either having cognitive decline or being cognitively intact.

2. The computer-readable non-transitory medium of claim 1, wherein the receiving the data indicative of cognitive decline in the person occurs one year or longer after the receiving inertial sensor data.

3. The computer-readable non-transitory medium of claim 2, wherein the generating the classifier function further comprises calculating a statistical parameter of the shank angular velocity data, and wherein the classifier function is further based on the statistical parameter of the shank angular velocity.

4. The computer-readable non-transitory medium of claim 3, wherein the inertial sensor data and additional inertial sensor data comprises data indicative of a walk ratio or a turn-end time during the QTUG test, the walk ratio being a ratio of (a) a time taken to stand and walk to a median turning point and (b) a time taken to walk back from the median turning point and sit to complete the test and the turn-end time being a time taken during the QTUG test to walk back from the median turning point and sit to complete the test.

5. The computer-readable non-transitory medium of claim 4, further comprising receiving an age of the person, wherein the generating the classifier function is further based on the age in addition to the received inertial sensor data and the determined indication of cognitive decline in the person and wherein the classifier function is configured to predict whether the another person will experience cognitive decline based on the another person's age and the collected inertial sensor data.

6. The computer-readable non-transitory medium of claim 5, further comprising receiving grip strength data of the person, wherein generating the classifier function is further based on the person's grip strength data, and wherein the classifier function is configured to predict whether the another person will experience cognitive decline further based on the another person's grip strength.

7. The computer-readable non-transitory medium of claim 1, wherein the received data indicative of cognitive function in the person comprises a follow-up mini-mental state exam (MMSE) score, the method further comprising: receiving a baseline MMSE score before receiving the follow-up MMSE score, wherein the determining the indication of cognitive decline in the person comprises determining a difference between the baseline MMSE score and the follow-up MMSE score, the difference between the scores being used to create the classifications in the generated classifier function of cognitive decline and cognitively intact.

8. A computer-readable non-transitory medium comprising computer-readable code physically embodied thereon which, when executed by a processor, causes the processor to perform a method comprising:
receiving baseline inertial sensor data directly from one or more inertial sensors attached to a person's shank that performs a quantitative timed-up-and-go (QTUG) test, the received baseline inertial sensor data being measured by the one or more inertial sensors and comprising shank angular velocity data related to the person sitting, walking, and turning;

receiving, at a time subsequent to the receiving baseline inertial sensor data, follow-up inertial sensor data from the person that performs the QTUG test directly from the one or more inertial sensors, the follow-up inertial sensor data comprising shank angular velocity data related to the person sitting, walking, and turning measured during a subsequent QTUG test;

determining a change between the baseline inertial sensor data and the follow-up inertial sensor data;

determining an indication of cognitive decline in the person based on the baseline inertial sensor data;

determining an indication of cognitive decline in the person based on the change;

generating a classifier function that associates the received baseline inertial sensor data and the determined change with the indication of cognitive decline in the person; then after generation of the classifier function, receiving other baseline inertial sensor data from another person that performs the QTUG test directly from the one or more inertial sensors;

receiving other follow-up inertial sensor data directly from the one or more inertial sensors from the another person that performs the QTUG test thereafter;

determining a change between the other baseline inertial sensor data and the follow-up inertial sensor data of the another person;

using the generated classifier function, associating the follow-up inertial sensor data and the determined change from the another person to an indication of cognitive decline in the another person; and providing, using the association of the generated classifier function, to a user an assessment of whether the another person has experienced cognitive decline based on the other baseline inertial sensor data and the other follow-up inertial sensor data collected from the another person, wherein the assessment provided to the user comprises a classification of the another person as either having cognitive decline or being cognitively intact.

9. The computer-readable non-transitory medium of claim 8, wherein the method further comprises receiving a follow-up mini-mental state exam (MMSE) score, the method further comprising receiving a baseline MMSE score before receiving the follow-up MMSE score, wherein the determining the indication of cognitive decline in the person further comprises determining a difference between the baseline MMSE score and the follow-up MMSE score, the difference between the scores being used to create the classifications in the generated classifier function of cognitive decline and cognitively intact.

10. The computer-readable non-transitory medium of claim 8, wherein the baseline inertial sensor data comprises a baseline X-axis shank angular velocity data or baseline Z-axis shank angular velocity data, wherein the follow-up inertial sensor data comprises a follow-up X-axis shank angular velocity data or follow-up Z-axis shank angular velocity data, wherein the determining the change comprises determining a change between a statistical parameter of the baseline X-axis shank angular velocity data or of the baseline Z-axis shank angular velocity data and a statistical parameter of the follow-up X-axis shank angular velocity data or of the follow-up Z-axis shank angular velocity data.

11. The computer-readable non-transitory medium of claim 10, wherein the baseline inertial sensor data further comprises a mean single support percentage, wherein the follow-up inertial sensor data comprises a follow-up single support percentage, and wherein the determining the change comprises determining a change between the baseline single support percentage and the follow-up single support percentage.

12. The computer-readable non-transitory medium of claim 11, wherein the classifier function is a regularized discriminant classifier function.

13. The computer-readable non-transitory medium of claim 8, wherein the receiving the follow-up data from the person occurs one year or longer after the receiving baseline inertial sensor data.

14. A system for predicting a cognitive decline in a person, the system comprising:

one or more inertial sensors attached to a person's shank and in communication with a processor; and a non-transitory storage medium operatively coupled to the processor, the storage medium having instructions disposed thereon, which when executed by the processor, cause the processor to:

receive inertial sensor data directly from one or more inertial sensors attached to a person that performs a quantitative timed-up-and-go (QTUG) test, including shank angular velocity data comprising measured gait parameters related to the person sitting, walking, and turning, receive, at a time subsequent to receiving the inertial sensor data from the QTUG test, additional inertial sensor data directly from the one or more inertial sensors including shank angular velocity data comprising gait parameters related to the person sitting, walking, and turning measured during a subsequent QTUG test, determine an indication of cognitive decline in the person based on a difference between the received inertial sensor data and the additional inertial sensor data, generate a classifier function that associates the received inertial sensor data with the indication of cognitive decline in the person;

after generation of the classifier function, collect inertial sensor data directly from the one or more inertial sensors from another person that performs the QTUG test;

use the generated classifier function to associate the collected inertial sensor data from the QTUG test from the another person to an indication of cognitive decline in the another person, and provide, using the association from the generated classifier function, to a user a prediction of whether the another person will experience cognitive decline based on the inertial sensor data collected from the another person, wherein the prediction provided to the user comprises a classification of the another person as either having cognitive decline or being cognitively intact.

15. The system of claim 14, wherein the additional inertial sensor data received by the processor occurs after a time period that is one year or longer after receiving inertial sensor data.

16. A system for predicting a cognitive decline in a person, the system comprising:

one or more inertial sensors attached to a person's shank that performs a quantitative timed-up-and-go (QTUG) test and that are in communication with a processor; and a non-transitory storage medium operatively coupled to the processor, the storage medium having instructions disposed thereon, which when executed by the processor, cause the processor to:

receive baseline inertial sensor data directly from the one or more inertial sensors, the received baseline inertial sensor data being measured by the one or more inertial sensors and comprising shank angular velocity data related to the person sitting, walking, and turning during the QTUG test;

receive directly from the one or more inertial sensors, at a time subsequent to receiving the baseline inertial sensor data, follow-up inertial sensor data from the person, the follow-up inertial sensor data comprising shank angular velocity data related to the person sitting, walking, and turning measured during a subsequent QTUG test, determine a change between the baseline inertial sensor data and the follow-up inertial sensor data, determine an indication of cognitive decline in the person based on the baseline inertial sensor data, determine an indication of cognitive decline in the person based on the change;

generate a classifier function that associates the received baseline inertial sensor data and the determined change in inertial sensor data with the indication of cognitive decline in the person, receive other baseline inertial sensor data directly from the one or more inertial sensors from another person that performs the QTUG test;

receive other follow-up inertial sensor data directly from the one or more inertial sensors from the another person that performs the QTUG test thereafter, and provide, using the association from the generated classifier function, to a user an assessment of whether the another person has experienced cognitive decline based on the other baseline inertial sensor data and the other follow-up inertial sensor data collected from the another person, wherein the assessment provided to the user comprises a classification of the another person as either having cognitive decline or being cognitively intact.

17. The system of claim 16, wherein the follow-up inertial sensor data received by the processor occurs after a time period that is one year or longer after receiving baseline inertial sensor data.

* * * * *